(12) United States Patent
Hogg et al.

(10) Patent No.: US 8,313,811 B2
(45) Date of Patent: *Nov. 20, 2012

(54) PLASMA ENHANCED POLYMER ULTRA-THIN MULTI-LAYER PACKAGING

(75) Inventors: Andreas Hogg, Neuchatel (CH); Herbert Keppner, Colombier NE (CH); Thierry Aellen, Neuchatel (CH); Juergen Burger, Neuchatel (CH)

(73) Assignee: Medos International S.A.R.L. (CH)

( * ) Notice: Subject to any disclaimer, the term of this patent is extended or adjusted under 35 U.S.C. 154(b) by 178 days.

This patent is subject to a terminal disclaimer.

(21) Appl. No.: 12/854,304

(22) Filed: Aug. 11, 2010

(65) Prior Publication Data

US 2011/0038130 A1     Feb. 17, 2011

Related U.S. Application Data

(60) Provisional application No. 61/233,395, filed on Aug. 12, 2009.

(51) Int. Cl.
 *B32B 3/00*     (2006.01)
 *B05D 3/00*     (2006.01)
 *C23C 16/50*    (2006.01)
 *H05K 5/00*     (2006.01)

(52) U.S. Cl. ........ 427/470; 361/751; 361/752; 361/757; 427/2.24; 427/457; 427/458; 428/68; 428/76

(58) Field of Classification Search .............. 428/76, 428/68; 361/751, 752, 757; 427/2.24, 457, 427/458

See application file for complete search history.

(56) References Cited

U.S. PATENT DOCUMENTS

| | | | |
|---|---|---|---|
| 4,206,762 A | 6/1980 | Cosman |
| 4,237,900 A | 12/1980 | Schulman |
| 4,281,667 A | 8/1981 | Cosman |
| 4,676,255 A | 6/1987 | Cosman |
| 4,954,925 A | 9/1990 | Bullis |
| 5,142,912 A | 9/1992 | Frische |
| 5,361,218 A | 11/1994 | Tripp |
| 5,444,901 A | 8/1995 | Wiegand |
| 5,609,629 A | 3/1997 | Fearnot |
| 5,629,008 A | 5/1997 | Lee |

(Continued)

FOREIGN PATENT DOCUMENTS

EP          992609 A1    4/2000

(Continued)

OTHER PUBLICATIONS

Ruckh, R. et al; Model Calculation of Polymer Heterostructures; Physica Scripta. 1988; pp. 122-124; vol. 38, Institute of Physics Publishing (IOP) on behalf of the Royal Swedish Academy of Sciences; Academies of Sciences and Physical Societies; Sweden.

(Continued)

*Primary Examiner* — Brent O'Hern

(57) ABSTRACT

An implantable medical device including a plurality of components on a substrate, and a biocompatible multi-layer polymeric coating applied by vapor deposition to conform to and sealingly cover at least a portion of the components and/or the substrate. The coating is applied in at least two pairs of layers, wherein each pair has one layer formed by dissociation of a precursor and then simple deposition of that precursor, and the other layer is formed by at least one of plasma dissociation and excitation of the precursor to form a plasma-enhanced precursor, and then deposition of the plasma-enhanced precursor.

11 Claims, 2 Drawing Sheets

U.S. PATENT DOCUMENTS

| | | | |
|---|---|---|---|
| 6,096,070 | A | 8/2000 | Ragheb |
| 6,144,106 | A | 11/2000 | Bearinger |
| 6,570,325 | B2 | 5/2003 | Graff |
| 6,635,014 | B2 | 10/2003 | Starkweather |
| 6,703,462 | B2 | 3/2004 | Lee |
| 6,709,715 | B1 | 3/2004 | Lang |
| 6,716,444 | B1 | 4/2004 | Castro |
| 6,774,278 | B1 | 8/2004 | Ragheb |
| 7,007,551 | B2 | 3/2006 | Zdeblick |
| 7,131,334 | B2 | 11/2006 | Mei |
| 7,334,480 | B2 | 2/2008 | Silverbrook |
| 7,347,826 | B1 | 3/2008 | Karicherla |
| 7,364,925 | B2 | 4/2008 | Lee |
| 7,413,547 | B1 | 8/2008 | Lichtscheidl |
| 7,464,598 | B2 | 12/2008 | Silverbrook |
| 7,580,754 | B2 | 8/2009 | Zhang |
| 7,611,533 | B2 | 11/2009 | Bates |
| 2002/0038134 | A1 | 3/2002 | Greenberg |
| 2002/0045921 | A1 | 4/2002 | Wolinsky |
| 2002/0172811 | A1 | 11/2002 | Barth |
| 2002/0185712 | A1 | 12/2002 | Stark |
| 2003/0036794 | A1* | 2/2003 | Ragheb et al. ............... 623/1.15 |
| 2004/0229051 | A1 | 11/2004 | Schaepkens |
| 2006/0083772 | A1 | 4/2006 | DeWitt |
| 2006/0111791 | A1 | 5/2006 | Forsell |
| 2006/0147492 | A1 | 7/2006 | Hunter |
| 2006/0173497 | A1 | 8/2006 | Mech |
| 2007/0096281 | A1 | 5/2007 | Greenberg |
| 2007/0128420 | A1 | 6/2007 | Maghribi |
| 2007/0158100 | A1 | 7/2007 | Greenberg |
| 2007/0216300 | A1 | 9/2007 | Lee |
| 2008/0051862 | A1 | 2/2008 | Mech |
| 2008/0132992 | A1 | 6/2008 | Bates |
| 2008/0185173 | A1 | 8/2008 | Bedinger |
| 2008/0200750 | A1 | 8/2008 | James |
| 2008/0306554 | A1 | 12/2008 | McKinley |
| 2009/0004241 | A1 | 1/2009 | Ho |
| 2009/0036754 | A1 | 2/2009 | Pons |
| 2009/0110892 | A1 | 4/2009 | Erlat |
| 2009/0124965 | A1 | 5/2009 | Greenberg |
| 2009/0142227 | A1 | 6/2009 | Fuchs |
| 2009/0192580 | A1 | 7/2009 | Desai |
| 2009/0254146 | A1 | 10/2009 | Bonmassar |
| 2009/0263581 | A1 | 10/2009 | Martin, III |
| 2009/0263641 | A1 | 10/2009 | Martin, III |
| 2009/0288876 | A1 | 11/2009 | Bedinger |
| 2009/0291200 | A1 | 11/2009 | Bedinger |
| 2009/0297813 | A1 | 12/2009 | Erlat |
| 2010/0005851 | A1 | 1/2010 | Cottles |
| 2011/0015686 | A1 | 1/2011 | Kara |
| 2011/0038130 | A1 | 2/2011 | Hogg |
| 2011/0038131 | A1 | 2/2011 | Hogg |
| 2011/0039050 | A1 | 2/2011 | Hogg |

FOREIGN PATENT DOCUMENTS

| | | | |
|---|---|---|---|
| WO | WO 2006063157 | A2 | 6/2006 |
| WO | WO 2008039543 | A1 | 4/2008 |

OTHER PUBLICATIONS

Sworecki, K. et al; Modification of Polymer Membranes by Ion Implantation; Nuclear Instruments and Methods in Physics Research; (2004); B 225; pp. 483-488; 2004 Elsevier B.V.

Kumar, R.; New Developments in Parylene Technology for Medical Electronics Advancement; Proceedings of the SMTA Medical Electronics Symposium; May 15-17, 2006; pp. 9; Bloomington. Minnesota. USA.

Affinito, J.D. et al; A New Method for Fabricating Transparent Barrier Layers; Thin Solid Films (1996); pp. 63-67; 290-291; 1996 Published by Elsevier Science S.A.

Nicholas, M.F. et al; Functional Hermetic Encapsulation of Integrated Circuits; ISA, 1991—pp. 331-339; Paper 091-043 0067-8856/91; ISA Publishing; Research Triangle Park, NC, USA; The British Library, UK.

North, B.; Intracranial Pressure Monitoring; Head Injury; 1997; pp. 209-216; 10; Chapman & Hall, London.

Khabari, A. et al: Partially Ionized Beam Deposition of Parylene; Journal of Non-Crystalline Solids (2005); pp. 3536-3541; vol. 351; 2005 Elsevier B.V.

Li, P.-Y, et al; A Parylene Bellows Electrochemical Actuator for Intraocular Drug Delivery; Transducers Jun. 21-25, 2009; pp. 1461-1464; 978-1-4244-4193-8/09; IEEE 2009, Piscataway, NJ, USA.

Pang, C.; Parylene Technology for Neural Probes Applications; Thesis for the Degree of Doctor of Philosophy; Sep. 17, 2007; pp. vii-viii and pp. 1-139; California Institute of Technology, Pasadena, CA, USA 2008.

Wolgemuth, L.; Parylenes: Advanced Polymers for Medical Devices; Specialty Coating Systems, 2006; pp. 1-4; 7645 Woodland Drive, Indianapolis, IN 46278 USA; lwolgemuth@scscoatings.com.

Zakar, E. et al; Patterning of Thick Parylene Films by Oxygen Plasma for Application as Exploding Foil Initiator Flyer Material; Army Research Laboratory; Sep. 2009; pp. 1-13; ARL-TR-4956; Adelphia, MD 20783-1197.

Callahan, R. et al.; Etching parylene-N using a remote oxygen microwave plasma; J. Vac. Sci. Technol. B, Sep./Oct. 2002; pp. vol. 20, No. 5; pp. 1870-1877; © 2002 American Vacuum Society.

Codman® ICP Monitoring System Quick set-up Guide; Product Brochure © 2001 Codman & Shurtleff, Inc.

Feili, D. et al.; Flexible organic field effect transistors for biomedical microimplants using polyimide and parylene C as substrate and insulator layers; J. Micromech. Microeng. (2006); pp. 1555-1561; 16; Institute of Physics Publishing.

Hambrecht, F.T.; Biomaterials research in neural prostheses; Biomaterials Jul. 1982; pp. 187-188, vol. 3; Butterworth & Co (Publishers) Ltd.

Hemedex® Cerebral Blood Flow Monitoring System; Product Brochure © 2007 Codman & Shurtleff, Inc.

Huang, Sheng-Jean, et al.; Clinical outcome of severe head injury using three different ICP and CPP protocol-driven therapies; Journal of Clinical Neuroscience (2006)pp. 818-822; 13; Elsevier Ltd.

ICP Express™; Product Brochure © 2001 Codman & Shurtleff, Inc.

Khabari, A., Partially ionized beam deposition of parylene; Journal of Non-Crystalline Solids (2005); pp. 3536-3541; 351; Elsevier B.V.

Lahann, J.; Vapor-based polymer coatings for potential biomedical applications; Polymer International (2006); pp. 1361-1370; 55; 2006 Society of Chemical Industry.

Lee, L. James; Polymer Nanoengineering for Biomedical Applications; Annals of Biomedical Engineering, Jan. 2006; pp. 75-88; vol. 34, No. 1.

Mark, Herman F.; Xylylene Polymers; Concise Encyclopedia of Polymer Science and Technology; 2007; pp. 1384-1389, John Wiley & Sons, USA 2007.

Mitu, B., et al; Plasma-deposited parylene-like thin films: process and material properties; Surface and Coatings Technology (2003), pp. 174-175; Issue 124-130; Elsevier Science B.V; www.sciencedirect.com.

Rodger, D.C.; et al.; Flexible parylene-based multielectrode array technology for high-density neural stimulation and recording; Sensors and Actuators B (2008); pp. 449-460; 132; Elsevier B.V.

Senkevich, J.J. et al.; The facile surface modification of poly(p-xylylene) ultrathin Films; Colloids and Surfaces A: Physicochem. Eng. Aspects; (2003); pp. 167-173; 216; Elsevier Science B.V.

Seymour, John P, et al; The insulation performance of reactive parylene films in implantable electronic devices; Biomaterials (2009); pp. 6158-6167; 30; Elsevier Ltd.

Wolgemuth, L.; A Look at Parylene Coatings in Drug-Eluting Technologies; Reprinted from Medical Device & Diagnostic Industry, Aug. 2005; Copyright © 2005 Canon Communications LLC.

Yamagishi, F. G.; Investigation of Plasma-Polymerized Films As Primers for Parylene-C Coatngs on Neural Prosthesis Materials; Metallurgical and Protective Layers Thin Solid Films, (1991) pp. 39 50; 202; Elsevier Sequoia/Printed in The Netherlands.

Yu, Qingsong et al.; Engineering the surface and interface of Parylene C coatings by low-temperature plasmas; Progress in Organic Coatings; (2001); pp. 247-253; 41; 2001 Elsevier Science B.V.

Balestreri, M. et al; Impact of Intracranial Pressure and Cerebral Perfusion Pressure on Severe Disability and Mortality After Head Injury; Neurocritical Care; 2006; pp. 8-13; vol. 04: Humana Pess Inc.; ISSN 1541-6933/06/4:8-13.

Bork, T. et al; Development and in-vitro characterization of an implantable flow sensing transducer for hydrocephalus; Biomedical Microdevices, vol. 12, No. 4, 607-618, DOI: 10.1007/s10544-010-9413-6; SpringerLink Date: Mar. 13, 2010.

Boyd, B.; Advanced coating technologies for lead-free solders; Global SMT & Packaging. Jun. 2007, pp. 10-12; www.globalsmt.net.

Callahan, Russell R.A. et al; Downstream oxygen etching characteristics of polymers from the parylene family; J. Vac. Sci. Technol. B, pp. 1496-1500; vol. 21, No. 4, Jul./Aug. 2003; © 2003 American Vacuum Society.

Chang, T.Y. et al; Cell and Protein Compatibility of Parylene-C Surfaces; Langmuir, 2007; pp. 11718-11725; vol. 23, No. 23; 2007 American Chemical Society Published on Web Oct. 4, 2007.

Chiang, C.C. et al; Deposition and permeation properties of SiNX/parylene multilayers on polymeric substrates; Surface & Coatings Technology 200 (2006) pp. 5843-5848; www.sciencedirect.com.

Czosnyka, M., et al; Monitoring and interpretation of intracranial pressure; J. Neurol. Neurosurg. Psychiatry 2004;75; pp. 813-821; Downloaded from jnnp.bmj.com on Sep. 2, 2009; DOI:10.1136/jnnp.2003.033126.

Czosnyka, M., et al; Monitoring of Cerebrovascular Autoregulation: Facts, Myths, and Missing Links; Neurocrit Care (2009) 10 pp. 373-386; Humana Press DOI 10.1007/s12028-008-9175-7.

Hsu, Jui-Mei et al.; Characterization of Parylene-C film as an encapsulation material for neural interface devices; 4M Network of Excellence, 4M Knowledge base—papers; Submitted on Nov. 12, 2007—16:23. http://www.4m-net.org/files/papers/4M2007/374451/PID374451.pdf.

Kokko, K., et al; Composite coating structure in an implantable electronic device; Soldering & Surface Mount Technology; vol. 21 No. 3 (2009); pp. 24-29 © Emerald Group Publishing Limited [ISSN 0954-0911].

Kumar, R: Advances in Adhesion Solutions for Medical Applications; Proceedings of the SMTA Medical Electronics Symposium, Jan. 29-31, 2008, Anaheim, California, USA; rkumar@scscoatings.com.

Pruden, K.G. et al; Characterization of Parylene-N and Parylene-C Photooxidation; Journal of Polymer Science: Part A: Polymer Chemistry, pp. 1486-1496; vol. 41, (2003) © 2003 Wiley Periodicals, Inc.

Pruden, K.G. et al; Ammonium chloride complex formation during downstream microwave ammonia plasma treatment of parylene-C; J. Vac. Sci. Technol. A, Nov./Dec. 2005; pp. 1605-1609; vol. 23, No. 6.

Sadhir, R.K.et al.; The adhesion of glow-discharge polymers, Silastic and Parylene to implantable platinum electrodes: results of tensile pull tests after exposure to isotonic sodium chloride; Biomaterials 1981, pp. 239-243, vol. 2, October.

Seong, J.W. et al; Effects of ion bombardment with reactive gas environment on adhesion of Au films to Parylene C film; Thin Solid Films 476 (2005) pp. 386-390; © 2004 Elsevier B.V.; www.sciencedirect.com.

Stieglitz, T., et al; Encapsulation of Flexible Biomedical Microimplants with Parylene C; Fraunhofer-Institute for Biomedical Engineering; thomas.stieglitz@ibmt.fhg.de; https://ifess.org/ifess02/stimulation_technology/StieglitzT1.pdf.

Tewari, P. et al; Control of interfaces on electrical properties of SiO2-Parylene-C laminar composite dielectrics; Journal of Colloid and Interface Science 332 (2009) pp. 65-73.

Von Elm, Erik, et al; Severe traumatic brain injury in Switzerland—feasibility and first results of a cohort study; SWISS MED WKLY 2008;138 (23-24): pp. 327-334 www.smw.ch.

Zhang, X., et al; Crystallinity properties of parylene-n. affecting its use as an ILD in submicron integrated circuit technology; Thin Solid Films 270 (1995) pp. 508-511; Elsevier Science S.A.

Affinito, John., et al; Vacuum deposited polymer / metal multilayer films for optical application; Thin Solid Films; (1995); pp. 43-48; vol. 270; © 1995 Elsevier Science S.A., US.

Blenkiewicz, J.; Plasma-Enhanced Parylene Coating for Medical Device Applications; Medical Device Technology; Jan./Feb. 2006; pp. 10-11; vol. 17. No. 1; www.medicaldevicesonline.com; US.

Charlson, E.M. et al; Temperature Selective Deposition of Parylene-C; IEEE Transactions on Biomedical Engineering; Feb. 1992; pp. 202-206; vol. 39, No. 2; IEEE, Piscataway, NJ US.

Chou, Chia-Man, et al; Preparation of Plasma-Polymerized Para-Xylene as an Alternative to Parylene Coating for Biomedical Surface Modification; Surface & Coatings Technology (2010); pp. 1631-1636; vol. 204; Elsevier Science B.V; www.elsevier.com/locate/surfcoat, US.

Dribinskiy, Stanislav F. et al; Properties of Various Polyparylenes Deposited by Chemical Vapor Deposition; Paper PS3-TuP12; AVS 53rd International Symposium; Nov. 14, 2006; pp. 1-4; University of Applied Sciences, D-80335 Munich and Plasma-Parylene Coating Services, D-83022 Rosenheim; DE.

Hardy, Alan; Protection for Complicated SMD Assemblies; Surface Mount Technology; Feb. 2008; pp. 1-2; PennWell Corporation, Tulsa, OK.

Heetderks, Wiluam J.; RF Powering of Millimeter- and Submillimeter-Sized Neural Prosthetic Implants; IEEE Transactions on Biomedical Engineering; May 1988; pp. 323-327; vol. 35, No. 5; IEEE, Piscataway, NJ US.

Meng, E. et al; Plasma Removal of Parylene C; J. Micromech. Microeng. (2008), pp. 1-13; 18 045004; IOP Publishing; http://iopscience.iop.org, US.

Mitu, B., et al; Plasma-Deposited Parylene-Like Thin Films: Process and Material Properties; Surface and Coatings Technology; (2003) pp. 124-130; 174-175; Elsevier Science B.V; www.sciencedirect.com, US.

Momentive Performance Materials: Silquest A-174* Silane Product Brochure; Copyright 2003-2007 Momentive Performance Materials Inc., Wilton, CT, USA.

Ratanalert, Sanguansin, M.D. et al; ICP Threshold in CPP Management of Severe Head Injury Patients; Surg. Neurol.; 2004; pp. 429-434; 61; © 2004 Elsevier Inc. 360 Park Avenue South, New York, NY 10010-17.

Ratier, Bernard; Vapor Deposition Polymerization and Reactive Ion Beam Etching of poly(p-xylylene) Films for Waveguide Applications; Optical Materials; (1999); pp. 229-233; vol. 12; 1999 Elsevier Science B.V.

Seymour, John P., et al; Neural Probe Design for Reduced Tissue Encapsulation in CNS; Biomaterials; (2007); pp. 3594-3607; vol. 28, Issue 25; doi:10.1016/j.biomaterials.2007.03.024; Copyright © 2007 Elsevier Ltd, US.

V&P Scientific, Inc; Solvent Resistance of Parylenes C,N,D; Technology Letter #10; Revised May 1985; Copyright © 2009, V&P Scientific, Inc. San Diego, CA; http://www.vp-scientific.com/solvent.htm.

Wolgemuth, Lonny; A Look at Parylene Coatings in Drug-Eluting Technologies; Medical Device & Diagnostic Industry; Aug. 1, 2005; Copyright © 2005 Medical Device & Diagnostic Industry.

Wolgemuth, Lonny; The Truly Conformal Coating; Medical Device Developments; Apr. 4, 2008; 2 pages; vol. 1; http://www.medicaldevice-network.com/features/feature1818/; Copyright 2011 Net Resources International US.

Wright, Dylan, et al; Reusable, Reversibly Sealable Parylene Membranes for Cell and Protein Patterning; Journal of Biomedical Materials Research Part A; May 2008; pp. 530-538; vol. 85A; Article first published online: Aug. 29, 2007; Copyright © 2007 Wiley Periodicals, Inc., A Wiley Company; http://onlinelibrary.wiley.com/doi/10.1002/jbm.a.31281/abstract.

Xingding, Zhang; The relationship between GCS, ICP, CPP and glutamate in the cerebrospinal fluid following acute cerebral injury and brain edema in humans; Head Injury—Pathophysiology of Head Injury; Jul. 7, 1997; p. S71; P-2-159.

* cited by examiner

PLASMA ENHANCED POLYMER ULTRA-THIN MULTI-LAYER PACKAGING

CROSS-REFERENCE TO RELATED APPLICATION

This application claims priority to U.S. Provisional Application No. 61/233,395 by Burger et al. filed Aug. 12, 2009 entitled "Ultrathin Multilayers for a Hermetic Packaging". The following applications, filed concurrently herewith, are incorporated herein by reference: U.S. patent application Ser. No. 12/854,298 entitled "Ultra-Thin Multi-Layer Packaging" by Hogg et al.; and U.S. patent application Ser. No. 12/854,320 entitled "Packaging with Active Protection Layer" by Hogg et al.

BACKGROUND OF THE INVENTION

1. Field of the Invention

The invention relates to hermetic biocompatible packaging and more particularly to packaging that is deposited in successive layers over three-dimensional structures.

2. Description of the Related Art

Packaging which is cost-effective and compatible with miniaturization is an important factor in the production of an implantable medical device. There is a need for a reliable, cost-effective batch-manufacturing packaging process such as a wafer level packaging, to protect components such as electronic- and mechanical components, micro-electronic- and mechanical systems, micro-electro-mechanical systems and substrates carrying such components. Such packaging must be mechanically and chemically stable to protect the body tissue from potentially toxic dissolvents, and also to protect the components of the implanted device from corrosion or degradation created by bodily fluids.

Encapsulation of organic light emitting diodes by at least one barrier stack is disclosed in U.S. Pat. No. 6,570,325 by Graff et al. The barrier stack includes at least one barrier layer and at least one decoupling layer. Other protective barriers which include parylene for opto-electronic devices are disclosed by Lee et al. in U.S. Patent Application Publication Nos. 2005/0146267, now U.S. Pat. Nos. 7,364,925, and 2007/0216300, now abandoned.

Techniques for protecting integrated circuits using copolymers formed of parylene N and co-monomers with various double bonds is disclosed by Lang et al. in U.S. Pat. No. 6,709,715. Other, more recent coating techniques utilizing parylene are disclosed by Bedinger et al. in U.S. Patent Application Publication No. 2009/0291200 and by Martin, III et al. in U.S. Patent Application Publication Nos. 2009/0263581 and 2009/0263641.

It is therefore desirable to provide improved hermetic biocompatible packaging, especially for implantable medical devices for which reduction of size is preferred.

SUMMARY OF THE INVENTION

An object of the present invention is to provide improved, lower-cost multi-layer packaging having low permeability to bodily fluids to protect both the patient and components beneath the packaging.

Another object of the present invention is to provide such packaging which can be applied to medical devices substantially at room temperature to protect the medical devices against temperature defects which may otherwise occur at higher application temperatures.

A still further object of the present invention is to provide such packaging which can be manufactured more rapidly and with fewer handling steps.

This invention features an implantable medical device including a plurality of components on a substrate, and a biocompatible multi-layer polymeric coating applied by vapour deposition to conform to and sealingly cover at least a portion of the components. The coating is applied in at least two pairs of layers, wherein each pair has one layer formed by dissociation of a precursor and then simple deposition of that precursor, and the other layer is formed by at least one of plasma dissociation and excitation of the precursor to form a plasma-enhanced-precursor and then deposition of the plasma-enhanced precursor.

In a number of embodiments, a barrier property for the transport of impurities is dominated more by the interface between two adjacent layers than by the thickness of each individual layer, and each layer differs in at least one diffusion barrier property from the other layer in the pair. In some embodiments, diffusion through each layer differs from that of the other layer in the pair. In certain embodiments, the precursor for at least one pair is selected from di-p-xylylene and halogenated derivatives thereof to form a type of parylene for each layer of the pair. In one embodiment, the multi-layer coating conforms to and sealingly covers at least substantially all of the components, some or all of which may be three-dimensional, and may cover some or all of the substrate as well.

BRIEF DESCRIPTION OF THE DRAWINGS

In what follows, preferred embodiments of the invention are explained in more detail with reference to the drawings, in which.

DETAILED DESCRIPTION OF THE PRESENTLY PREFERRED EMBODIMENTS

Figure 1:
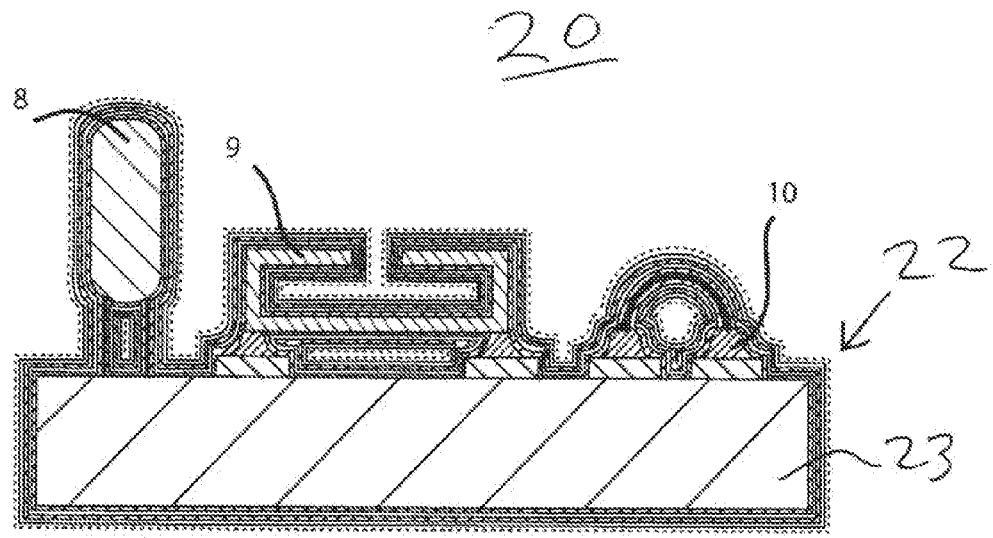
FIG. 1 is a schematic cross-sectional view of complex, three-dimensional components and a substrate coated with multiple layers according to the present invention.

FIG. 1 illustrates an example of components and a substrate of an implantable medical device 20 with three dimensional conformal packaging according to the present invention. Device 20 includes a plurality of three-dimensional components, such as transistor 8, micro-electro-mechanical system 9 and conductive bonding 10, on a substrate 23 which can be flexible or rigid as desired. A biocompatible multi-layer coating 22 applied by vapour deposition conforms to and sealingly covers at least a portion of the components 8,9,10 and the substrate 23.

Figure 2:
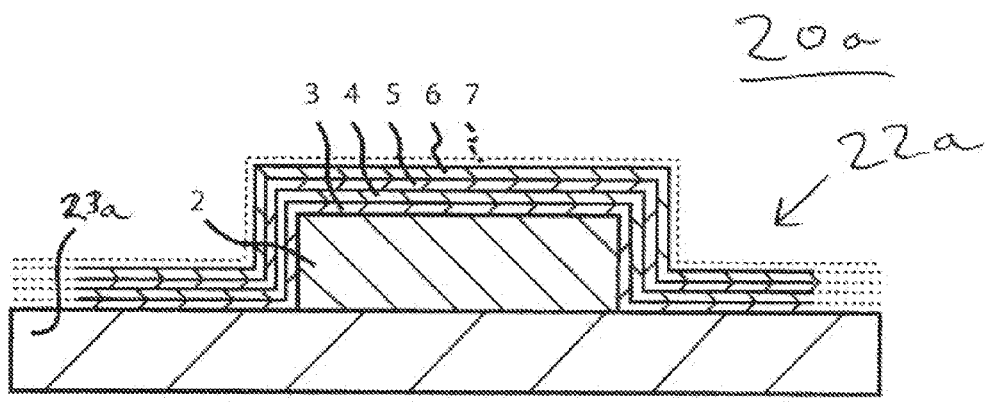
FIG. 2 is an enlarged cross-sectional view of multiple layers according to the present invention protecting a component on a substrate.

The coating 22 is applied in at least two pairs of layers, wherein each pair has one layer formed by dissociation of a precursor and then simple deposition of that precursor, and the other layer is formed by at least one of plasma dissociation and excitation of the precursor to form a plasma-enhanced precursor, and then deposition of the plasma-enhanced precursor. As illustrated schematically in FIG. 2, coating 22a is formed in a series of layers 3, 4, 5, and 6 over component 2 of device 20a with substrate 23a. Additional layers 7, 7' (not shown) et cetera can be added as desired. At least two pairs of layers, such as layers 3 plus 4 and 5 plus 6, have one layer each, such as layers 4 and 6, that have been plasma enhanced as described below.

In some constructions, the barrier property for the transport of impurities, such as unwanted molecules, atoms or ions, both inward toward a packaged device as well as outward toward a patient in which the device is implanted, is dominated more by the interface between two adjacent layers than by the thickness of each individual layer. Preferably, the diffusion behaviour of each layer is additive to that of the other layers As many pairs of layers can be applied as desired, with one or more additional layers between pairs as desired. In some constructions, an additional treatment, such as a gas plasma, or an additional layer is added to improve the interface between two layers, especially with respect to impurity diffusion.

It is a realization of the inventors that increasing the number and type of thinner layers, rather than having fewer, thicker layers, enhances overall barrier properties of packaging according to the present invention due to the increased number of layer interfaces. In other words, the sum of the interfaces dominates diffusion behaviour, and therefore the overall barrier effect of the coating, more than the sum of the thicknesses of the layers. This may also be expressed as the diffusion barrier being composed by each layer interface and each layer itself. Polymers such as parylene are especially desirable for being pin-hole free, homogenous, and stressless, and plasma-enhanced polymers are especially desirable for their higher density.

Figure 3:
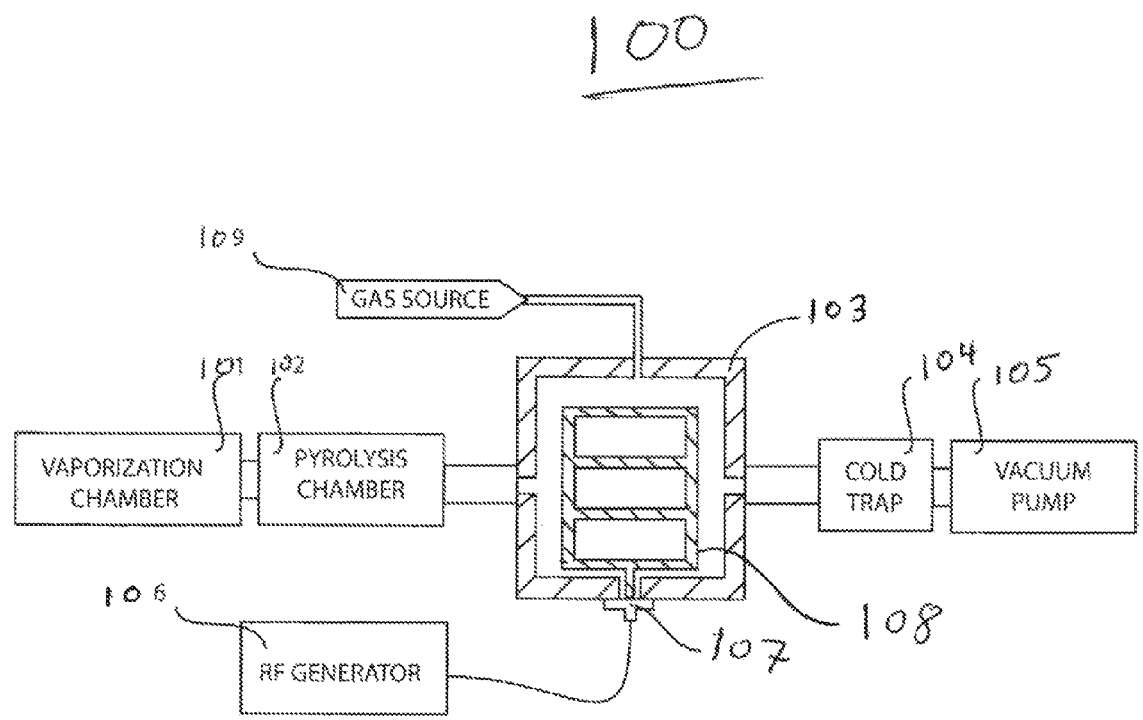
FIG. 3 is a schematic diagram of a reactor system for producing multi-layer packaging according to the present invention.

One system 100 for achieving such conformal packaging with multi-layer coatings is shown in FIG. 3. Deposition chamber 103 can be utilized for a thermal process, such as a conventional Gorham process, or a plasma enhanced process. For the thermal process, such as for parylene deposition, a vaporization chamber 101 is provided to vaporize a solid parylene precursor, for example a stable di-cyclic dimer, di-p-xylylene, or a halogenated derivative at temperature between 110° and 200° C. The vaporized precursor then passes to a pyrolysis chamber 102 to decompose the dimer in reactive species, such as monomers, at temperatures between 400° C. and 700° C. For dichloro-p-xylylene, typical parameters are 150° C. for the vaporization and 650° C. for the pyrolysis. The pyrolyzed precursor then passes from the pyrolysis chamber to the medical devices to be treated on a sample holder 108 in the deposition chamber 103. Typical parylene layer thickness is between 10 nm-100 microns. The precursor vapour pressure in the deposition chamber 103 is approximately between 1 and 10 Pa, typically 7 Pa, and the substrate temperature is substantially at room temperature. The remaining vapour mixture then passes from deposition chamber 103 to a cold trap 104 connected to a vacuum pump 105.

For the in-situ plasma process, controlled plasma is formed adjacent to the medical device wafers by RF energy applied to sample holder 108 from RF generator 106, with the deposition chamber 103 grounded, via a high frequency sealed pass-through connector 107. RF generator 106 can supply a high RF frequency of typically 13.56 MHz or 2.45 GHz to the sample holder 108 to enhance the decomposition and/or excitation of reactive species introduced into chamber. A gas source 109 is connected to deposition chamber 103 to introduce one or more gases in the plasma process, for substrate adhesion, surface treatment or precursor interaction, such as excitation, recombination or dissociation.

In a number of constructions of multi-layer coatings according to the present invention, RF generator 106 is periodically switched between an on state and an off state to create plasma conditions or not within deposition chamber 103. This switching can be coordinated with gas delivery from gas source 109. The periodic switching is sequential in some constructions and is interrupted in other constructions by the introduction of one or more barrier layers or adhesion layers. Typical parylene and plasma-enhanced parylene layer thickness is between 10 nm-100 microns for each layer.

The typical starting material for making parylene polymers is a stable cyclic dimer, di-p-xylylene, or halogenated derivative, which is available in solid form. The term parylene is well defined, for example, by Lee et al. in U.S. Patent Application Publication No. 2007/0216300, such as in paragraphs [0017] and [0018]. The inventors currently prefer di-chloro p-xylylene, also known as Parylene C.

Layer on substrate adhesion or layer on layer adhesion could be improved by different processes. Typically for parylene adhesion, either on substrate or on layer, but not limited to, silanization or gas plasma treatment are used. For example oxygen, nitrogen or air plasma is applied directly in the deposition chamber 103 before coating. Further, other adhesion layer or plasma enhanced deposition layer can be used. Preferably, a well known adhesion layer based on silanes are composed of vinyl trichlorosilane in either xylene, isopropyl alcohol or a chlorofluorocarbon gas. Alternatively, gammamethacryloxypropyltrimethoxysilane in a methanol-water solvent have been successfully used. Silanes can also be vapour phase applied if non-liquid application is preferred.

Thus, while there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

Every issued patent, pending patent application, publication, journal article, book or any other reference cited herein is each incorporated by reference in their entirety.

What is claimed is:

1. A method of making an implantable medical device comprising:
    placing a plurality of components on a substrate; and
    coating a biocompatible multi-layer polymeric applied by vapour deposition to conform to and sealingly cover at least a first portion of the components and the substrate, the coating being applied in at least two pairs of layers, wherein each pair has one layer formed by dissociation of a precursor and then simple deposition of that precursor, and the other layer is formed by at least one of plasma dissociation and excitation of the precursor to form a plasma-enhanced precursor, and then deposition of the plasma-enhanced precursor.

2. The method of making an implantable medical device of claim 1 wherein each layer differs in at least one diffusion barrier property from the other layer in the pair and adds to an overall barrier effect of the coating.

3. The method of making an implantable medical device of claim 1 wherein diffusion through each layer differs from that of the other layer in the pair.

4. The method of making an implantable medical device of claim 1 wherein a barrier property for the transport of impurities is dominated more by the interface between adjacent layers than by the thickness of each individual layer.

5. The method of making an implantable medical device of claim 1 wherein the precursor for at least one pair is selected from di-p-xylylene and halogenated derivatives thereof.

6. The method of making an implantable medical device of claim 5 wherein the precursor is dichloro-p-xylylene.

7. The method of making an implantable medical device of claim 1 wherein the components have at least a first three-dimensional portion, and the coating conforms to and sealingly covers at least the first portion of the components.

8. The method of making an implantable medical device of claim 7 wherein the multi-layer coating conforms to and sealingly covers at least substantially all of the components and the substrate.

9. A method of making an implantable medical device comprising:
   placing a plurality of components on a substrate having at least a first three-dimensional portion; and
   coating a biocompatible multi-layer polymeric applied by vapour deposition to conform to and sealingly cover at least a first portion of the components and the substrate, the coating being applied in at least two pairs of layers, wherein each pair has one layer formed by dissociation of a precursor and then simple deposition of that precursor, and the other layer is formed by at least one of plasma dissociation and excitation of the precursor to form a plasma-enhanced precursor, and then deposition of the plasma-enhanced precursor, wherein diffusion through each layer differs from that of the other layer in the pair, and the precursor for at least one pair is selected from di-p-xylylene and halogenated derivatives thereof.

10. The method of making an implantable medical device of claim 9 wherein the multi-layer coating conforms to and sealingly covers at least substantially all of the components and the substrate.

11. The method of making an implantable medical device of claim 10 wherein a barrier property for the transport of impurities is dominated more by the interface between adjacent layers than by the thickness of each individual layer.

* * * * *